(12) United States Patent
Lichtenberg et al.

(10) Patent No.: US 6,464,764 B1
(45) Date of Patent: Oct. 15, 2002

(54) PROTECTIVE AGENTS FOR WOOD

(75) Inventors: Florian Lichtenberg, Grenzach-Wyhlen; Hans-Norbert Marx, Bühl, both of (DE)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/601,470

(22) PCT Filed: Jan. 27, 1999

(86) PCT No.: PCT/CH99/00035

§ 371 (c)(1), (2), (4) Date: Oct. 4, 2000

(87) PCT Pub. No.: WO99/39886

PCT Pub. Date: Aug. 12, 1999

(30) Foreign Application Priority Data

Feb. 6, 1998 (CH) ................................. 0292/98

(51) Int. Cl.$^7$ ............................ A01N 33/02; B27K 3/50
(52) U.S. Cl. ................. 106/18.32; 106/15.05; 106/18; 514/642; 514/663; 514/673; 514/674; 514/740; 427/421; 427/428; 427/439; 427/440; 427/441; 427/442
(58) Field of Search ................... 106/18.32, 15.05, 106/18; 514/642, 663, 673, 674, 740; 427/421, 428, 439, 440, 441, 442

(56) References Cited

U.S. PATENT DOCUMENTS 3,617,314 A  11/1971  Hill .................. 106/2
5,013,748 A  5/1991  Radtke et al. .............. 514/383

FOREIGN PATENT DOCUMENTS

| CA | 2078412 | 3/1993 |
|---|---|---|
| DE | 195 35 664 | 4/1997 |
| EP | 0328466 | 8/1989 |
| EP | 0515899 | 12/1992 |
| EP | 0533016 | 3/1993 |
| FR | 2502054 | 9/1982 |

OTHER PUBLICATIONS

Derwent Abstract No. 1979–15227B, abstract of Soviet Union Patent Specification No. 601161 (Jun. 1978).*

* cited by examiner

*Primary Examiner*—Anthony J. Green
(74) *Attorney, Agent, or Firm*—Fisher, Christen & Sabol

(57) ABSTRACT

Solvent-free coating materials and treating agents used as water-based wood or material protective agents containing emulsifiable binding agents, quaternary ammonium compounds and optional additional active agents. The wood or material protective agents are non-flammable and enable a uniform distribution of the binding agent and the quaternary ammonium compounds in the substrates. As a result, the quaternary ammonium compounds function as a dissolving mediator for the binding agents which are dispersed in water without opacifying effects and are used as a biocide. The agents can additionally absorb water-insoluble organic biocides without impairing the homogeneity or stability of the formulation of the homogeneity of the distribution in the substrate.

26 Claims, No Drawings

PROTECTIVE AGENTS FOR WOOD

BACKGROUND OF THE INVENTION

1. Field of the Invention

The present invention relates to coating materials and treatment compositions for protecting wood and/or cellulosic substrates against biological material destruction, to a process for preparing the coating materials and treatment compositions, and to a method of using them.

2. Background Art

To reduce the environmental impact of organic solvents in coating materials, it is state of the art to use binders which are dispersible or emulsifiable in water. Especially for coating materials which are used on wood or wood materials, modified drying oils (e.g. linseed oil, soya oil, etc.) or correspondingly modified alkyd resins are available. The emulsifiability of such oils or alkyd resins is achieved by adding emulsifiers or, in a more elegant way, by incorporating hydrophilic groups into the binder molecule by means, for example, of transesterification with dicarboxylic or polycarboxylic acids and/or reaction with polyalcohols, polyethylene glycols, ethylene oxide, etc. The incorporation of hydrophilic groups leaves the film-forming properties of the oils and alkyd resins substantially unaffected.

The oils and alkyd resins with hydrophilic groups in the molecule have the advantage over the systems with added emulsifier that following oxidative drying the emulsifier cannot be washed out and hence neither the removal of active substances (e.g. substances acting against fungi and/or insects) nor the weather resistance are adversely affected by the free emulsifier.

Irrespective of whether a separate emulsifier is added to the systems or hydrophilic groups are incorporated into the oil or alkyd resin molecules, a general problem which arises with the known water-based treatment compositions and coating materials is that the ready-to-use emulsions have a limited life. Prolonged standing of the preparations is accompanied by instances of phase separation, creaming, or sedimentation of the heavier constituents, with reemulsification not always being an option.

A further disadvantage of the known emulsions and dispersions, especially those comprising biocidal active substances, is their poor penetration capacity into wood and wood materials. The active substances and additives tend to be situated in the dispersed organic phase, which accumulates near the surface, while only the dispersion medium, i.e. the water, penetrates into deeper layers. Homogeneous distribution of active substances, for example substances acting against rot, blue stain or insects, is virtually impossible to achieve with these systems and they biocidal activity is lost as soon as the surface is removed or damaged.

BROAD DESCRIPTION OF THE INVENTION

It was therefore an object of the present invention to provide storage-stable water-based treatment compositions and coating materials whose biocidal active substances penetrate effectively into wood or similar materials.

In accordance with the invention, this object is achieved by means of the coating materials, treatment compositions, method and process of the invention.

It has surprisingly been found that the abovementioned disadvantages of the known coating materials and treatment compositions may be eliminated by adding biocidal primary, secondary or tertiary amines or their salts or quaternary ammonium salts or mixtures of the aforementioned amines and/or salts to the aqueous emulsions of natural or synthetic oils, alkyd resins based on natural or synthetic oils, or mixtures of the aforementioned binders. The amines and ammonium salts that may be used in accordance with the invention possess at least one alkyl group having 6 to 24 carbon atoms, preferably having 8 to 18 carbon atoms. In the present case, primary amines include those which in addition to one or more primary amino groups also contain one or more secondary and/or tertiary amino groups in the molecule. The coating materials and treatment compositions of the invention contain from 2 to 50%, preferably from 5 to 25%, of binder(s) and from 0.5 to 40%, preferably from 1 to 10%, of amines and/or ammonium salts. Hereinbelow, all percentages, unless otherwise defined, are by mass and relate to the total composition. The term "alkyl group" embraces both linear and branched groups having the particular number of carbon atoms stated.

DETAILED DESCRIPTION OF THE INVENTION

For example, an emulsion containing 15 parts of binder (oil or alkyd resin with hydrophilic groups in the molecule) and 85 parts of water becomes clear following the addition of 5 parts of DDAC (didecyldimethylammonium chloride) and after brief stirring; any turbidity disappears, and a completely transparent solution is formed. Even years of storage, fluctuating temperatures, and freezing and thawing of the system are not accompanied by any phase separation or separation of components.

Examples of suitable amines for the coating materials and treatment compositions of the invention are the following:

as primary amines: $C_{8-18}$-alkylamines, N-($C_{8-18}$-alkyl)ethylenediamines, N-($C_{8-18}$-alkyl)propylenediamines, N,N-bis(2-aminoethyl)-$C_{8-18}$-alkylamines, or N,N-bis(3-aminopropyl)-$C_{8-18}$-alkylamines; as secondary amines: methyl- or ethyl-$C_{8-18}$-alkylamines; and as tertiary amines: dimethyl($C_{8-18}$-alkyl)amines. Examples of suitable salts of the amines are the halides, especially the chlorides and bromides, and the salts with organic acids. Organic acids hereinbelow are especially linear or branched $C_{1-6}$ carboxylic acids such as, for example, formic acid, acetic acid, propionic acid, butyric acid or isobutyric acid, and also hydroxy acids such as, for example, glycolic acid, lactic acid, malic acid or tartaric acid, or else sulphonic acids such as, for example, methanesulphonic acid, benzenesulphonic acid or toluenesulphonic acid.

The systems of the invention penetrate rapidly and deeply into wood and wood materials; no partial concentration differences can be found in the wood. The uniform penetration of all ingredients of the systems of the invention, comprising binder, cationic compounds and water, is surprising, since it is known that cationic compounds such as ammonium salts alone show little or no penetration into wood or comparable substrates, with the result that the biocidal activity of quaternary ammonium compounds applied from aqueous solutions, this activity being known per se, is normally restricted to the near-surface regions of the substrates. The present invention, therefore makes it possible to prepare preparations which are solvent-free, possess long-term stability (storage life), are transparent, and display penetration into wood and wood materials comparable with that of solventborne systems, combined with uniform distribution of all ingredients and good coating activity and processability.

Preferably, the coating materials and treatment compositions of the invention comprise a quaternary ammonium salt as biocidal component.

Examples of suitable quaternary ammonium salts are the following:

dimethyldi($C_{8-18}$ alkyl)ammonium halides, dimethyldi ($C_{8-18}$ alkyl)ammonium salts of organic acids, trimethyl($C_{8-18}$ alkyl)ammonium halides, trimethyl($C_{8-18}$ alkyl)ammonium salts of organic acids, dimethyl($C_{8-18}$ alkyl)benzylammonium halides, dimethyl($C_{8-18}$ alkyl)benzylammonium salts of organic acids, 1,1'-dimethyl-4,4'-bipyridinium halides, and di($C_{8-18}$ alkyl) methylpolyoxyethylammonium salts of organic acids, the terms "$C_{8-18}$ alkyl" and "organic acid" having the definitions given above.

Water-emulsifiable binders used are preferably oxidatively drying oils or alkyd resins.

In order to improve and supplement the biocidal activity, further biocides may be added to the coating materials and treatment compositions of the invention. For example, from 0.01 to 10% of the following active substances, alone or as a mixture, may be added: amphosurfactants having biocidal activity methyl benzimidazol-2-ylcarbamate 1,2-benzisothiazol-3-one biguanides having biocidal activity organic and inorganic boron derivatives α- tert-butyl-α-(p-chlorophenethyl)-1H-1,2,4-triazole-1-ethanol 2-sec-butylphenyl N-methylcarbamate (±)-cis-4-[3-(tert-butylphenyl)-2-methylpropyl]-2,6-dimethylmorpholine 5-chloro-2-methyl-4-isothiazolin-3-one 2-(4-chlorophenyl)-3-cyclopropyl-1-(1H-1,2,4-triazol-1-yl)butan-2-ole 1-(6-chloro-3-pyridinyl)methyl-4,5-dihydro-N-nitro-1H-imidazol-2-amine chlorhexidine and its salts chlorinated phenols such as tetra- or pentachlorophenol, for example chloronitrobenzene derivatives 1-[4-(2-chloro-α,α,α-trifluoro-p-tolyloxy)-2-fluorophenyl]-3-(2,6-difluorobenzoyl)urea 1-(4-chlorophenyl)-3-(2,6-difluorobenzoyl)urea α-[2-(4-chlorophenyl)ethyl]-α-(1,1-dimethylethyl)-1H-1,2,4-triazole-1-ethanol (RS) -α-cyano-3-phenoxybenzyl (RS)-2-(4-chlorophenyl)-3-methylbutyrate α-cyano-3-phenoxybenzyl 2-isopropyl-4-chlorophenylacetate N-cyclohexyl-N-methoxy-2,5-dimethylfuran-3-carboxamide di(guanidinooctyl)amine 1-[2-(4-dichlorophenyl)-1,3-dioxolan-2-yl]methyl]-1H-1,2,4-triazole 1-[2-(2,4-dichlorophenyl)-4-propyl-1, 3-dioxolan-2-ylmethyl)-1H-1,2,4-triazole 3-phenoxybenzyl (+)-3-(2,2-dichlorovinyl)-2,2-dimethylcyclopropan-1-carboxylate a-cyano-3-phenoxybenzyl 3-(2,2-dichlorovinyl)-2,2-dimethylcyclopropane-1-carboxylate α-cyano-3-phenoxybenzyl (1R,3R)-3-(2,2-dibromovinyl)-2,2-dimethylcyclopropane-1-carboxylate α-cyano-4-fluoro-3-phenoxybenzyl 3-(2,2-dichlorovinyl)-2,2-dimethylcyclopropane-1-carboxylate O,O-diethyl O-(α-cyanobenzylidenamino)thiophosphate O,O-diethyl O-3,5,6-trichloro-2-pyrridylthionophosphate O,O-diethyldithiophosphoryl-6-chlorobenzoxazolone 5,6-dihydro-2-methyl-1,4-oxathiin-3-carboxanilide N,N-dimethyl-N'-phenyl(N'-fluoromethylthio)sulfamide N,N-dimethyl-N'-tolyl(N'-fluoromethylthio)sulfamide O,O-dimethyl S-(2-methylamino-2-oxoethyl)dithiophosphate O,O-dimethyl S-(N-phthalimido)methyldithiophosphate 3,5-dimethyltetrahydro-1,3,5-thiadiazine-2-thione dimethylalkylammonium salts dithiocarbamates with metal or ammonium cations ethyl 2-(4-phenoxyphenoxy)ethylcarbaamate 2-(2-furyl)-1H-benzimidazole haloacetic acids and their amides land esters 6,7,8,9,10,10-hexachloro-1,5,5a,6,9,9a-hexahydro-6,9-methano-2,4,3-benzodioxathiepin 3-oxide hexachlorocyclohexane 8-hydroxyquinoline and its halogenated derivatives copper 8-oxyquinoline 2-iodobenzanilide 3-iodo-2-propynyl butylcarbamate 1-naphthyl N-methylcarbamate 2-methyl-4-isothiazolin-3-one methylene bisthiocyanate nitroalkanols with biocidal activity N-nitroso-N-cyclohexylhydroxylamine and its salts N-nitroso-N-phenylhydroxylamine and its salts norbornene dimethanohexachlorocyclosulfite 2-n-octyl-4-isothiazolin-3-one and its halogen derivatives organotin compounds, such as tributyltin oxide and tributyltin benzoate, for example phenylphenols 2-isopropoxyphenyl N-methylcarbamate N-propyl-N-[2-(2,4,6-trichlorophenoxy)ethyl]imidazole-1-carboxamide pyridine-2-thiol 1-oxide and its salts salicylanilide and halogenated derivatives (4-ethoxyphenyl)[3-(4-fluoro-3-phenoxyphenyl)propyl] dimethylsilane.

N-(1,1,2,2-tetrachloroethylthio)-3,6,7,8-tetrahydrophthalimide tetrachloroisophthalonitrile 2-(4-thiazolyl)benzimidazole 2-(thiocyanomethylthio)benzothiazole 1-(1,2,4-triazol-1-yl)-1-(4-chlorophenoxy)-3,3-dimethylbutan-2-one 1-(1,2;4-triazol-1-yl)-1-(4-chlorophenoxy)-3,3-dimethylbutan-2-one N-trichloromethylthio-3,6,7,8-tetrahydrophthalimide N-trichloromethylthiophthalimide N-tridecyl-2,6-dimethylmorpholine Moreover, the coating materials and treatment compositions of the invention may if desired comprise auxiliaries and additives for the purpose, for example, of hydrophobicization, protection, against UV light, protection against ageing, for the purpose of colouring and decoration, or to promote adhesion for the remainder of the coating system.

A process for preparing the coating materials and treatment compositions of the invention comprises first mixing binder(s) and biocidal amine and/or ammonium salt and then adding the water. In this case it is possible, if desired, for further organic active substances (fungicides, insecticides, bactericides, algicides, herbicides, etc.) to be dissolved in the binder/amine mixture without precipitating or crystallizing on the subsequent addition of water. It is therefore possible to obtain transparent and sediment-free preparations containing organic active substances in quasi-dissolved form without the need for organic solvents or solubilizers (such as glycol derivatives, for example) to be, present therein. For protecting wood and/or cellulosic substrates against biological material destruction, the coating materials and treatment compositions of the invention may be applied by brushing, rolling, spraying or dipping to the substrate that is to be protected.

The examples which follow illustrate the performance of the invention, without constituting any restriction.

In the examples, the following emulsifiable binders were used: (the percentages are by mass and relate to the total binder composition)

Binder A
95% linseed oil alkyd resin (oil length 90%), 5% coconut fatty alcohol ethoxylate (12 EO groups)

Binder B
95% soya alkyd resin (oil length 85%), 5% p-nonylphenol ethoxylate (9 EO groups)

Binder C
94% linseed oil, 3% maleic acid, 3% polyethylene glycol (10 EO groups). Preparation: linseed oil is heated to 180° C. with maleic acid and then esterified with polyethylene glycol at 195° C.

Binder D
92% soya oil, 3% maleic acid, 5%, polypropylene glycol (12 PO groups). Preparation: soya oil is heated to 180° C. with maleic acid and then esterified with polypropylene glycol at 170° C.

Binder E
85% polybutadiene oil ($C_{12}$ to $C_{20}$ chain length), 5% maleic acid, 10% polyethylene glycol (10 EO groups) Preparation: polybutadiene oil is !heated to 150° C. with maleic acid and the reaction product is esterified with polyethylene glycol at 150° C.

Binder F
80% linseed oil, 12% neopentyl glycol, 8% ethylene oxide. Preparation: linseed oil is reacted at 170° C. with neopentyl glycol and the reaction product is ethoxylated with ethylene oxide under pressure.

The binders described by way of example above, in the absence of further additives, give typical opaque (milky) emulsions with water (1:10). Binders A and B include a separate emulsifier, binders C to F include hydrophilic (emulsifying) groups in the molecule.

EXAMPLE 1

10.0% binder C
10.0% didecyldimethylammonium chloride (50% strength in water)
0.8% propiconazole
79.2% water

EXAMPLE 2

15.0% binder D
6.0% dimethyl($C_{8-18}$ alkyl)benzylammonium chloride (80% strength in water)
0.5% iodopropinyl butylcarbamate
0.5% tebuconazole
78.0% water

EXAMPLE 3

20.0% binder E
15.0% didecyldimethylammonium chloride (40% strength in water)
2.0% tri-n-butyltin oxide
63.0% water

EXAMPLE 4

10.0% binder C
10.0% didecyldimethylammonium lactate (40% strength in water)
0.2% silafluofen
0.4% carboxin
0.4% iodopropinyl butylcarbamate
79.0% water

EXAMPLE 5

20.0% binder C
10.0% N,N-didecyl-N-methyl-N-poly((oxyethyl) ammonium propionate (1–5 oxyethyl groups; 70% strength in water)
1.0% cyproconazole
69.0% water

EXAMPLE 6

10.0% binder F
10.0% $C_{8-18}$ alkyltrimethylammonium chloride (50% strength in water)
2.0% prochloraz
0.2% silafluofen
1.0% Neozapon yellow
76.8% water

EXAMPLE 7

12.0% binder C
10.0% didecyldimethylammonium chloride (50% strength in water)
1.0% tebuconazole
1.0% UV absorber (benzophenone derivative)
1.0% defoamer (silicone)
1.0% soluble azo dye, green
74.0% water

COMPARATIVE EXAMPLE 1

Not According to the Invention 10.0% binder A
5.0% butyl diglycol
0.8% propiconazole
84.2% water

COMPARATIVE EXAMPLE 2

Not According to the Invention 15.0% binder C
1.0% tebuconazole 10.0% diethylene glycol
74.0% water

COMPARATIVE EXAMPLE 3

Not According to the Invention 10.0% alkyd resin, soya oil type
0.5% dichlofluanid
1.0% tebuconazole
10.0% dipropylene glycol monomethyl ether
78.5% white spirit (b.p. 180–220° C.)

The properties of the exemplary formulations and their penetration behaviour and their protective activity against pathogenic fungi on pinewood are summarized in Table 1 below.

TABLE 1

| Example | trans-parent[1] | stab-ility[2] | solvent[3] | flamma-able[4] | pene-tration depth[5] | protec-tion[6] |
|---------|-----------------|---------------|------------|----------------|----------------------|----------------|
| 1  | + | + | − | − | 3–6 mm | ++ |
| 2  | + | + | − | − | 4–6 mm | ++ |
| 3  | + | + | − | − | 2–4 mm | ++ |
| 4  | + | + | − | − | 4–5 mm | ++ |
| 5  | + | + | − | − | 2–3 mm | ++ |
| 6  | + | + | − | − | 4–6 mm | ++ |
| 7  | + | + | − | − | 4–7 mm | ++ |
| C1 | − | − | + | − | 0–1 mm | + |
| C2 | − | − | + | − | 0–2 mm | + |
| C3 | + | + | + | + | 4–6 mm | + |

[1] + = no visible turbidity, no phase separation | − = urbidity and/or phase separation
[2] 4 months' storage at 50° C.: + = stable (no turbidity, no phase separation, no change in viscosity, no discoloration) | − = unstable
[3] + = contains organic solvents | − = no organic solvents
[4] + = flammable | − = nonflammable (no measurable flash point)
[5] in pine sapwood, application rate 200 g/m²
[6] test in accordance with DIN EN 113 (surface method) at 100 g/m² application rate (four types of fungus); ++ = high | + = moderate

What is claimed is:

1. A coating material or treatment composition for protecting wood and/or cellulosic substrates against biological material destruction, consisting of:
   (i) from 2 to 50 percent of a water-emulsifiable binder selected from the group consisting of (a) water-emulsifiable natural oils, (b) water-emulsifiable synthetic oils, (c) water-emulsifiable alkyd resins based on natural oils, (d) water-emulsifiable alkyl resins based on synthetic oils, and (e) mixtures of at least two of binders (a), (b), (c) and (d);
   (ii) from 0.5 to 40 percent of a biocidal component that is at least one quaternary ammonium salt, the quaternary ammonium salt having at least one alkyl group having 6 to 24 carbon atoms;
   (iii) optionally, from 0.01 to 10 percent of at least one biocidal agent other than biocidal component (ii) and other than a primary, secondary or tertiary amine or salts thereof;
   (iv) optionally, at least one auxiliary or additive member selected from the group consisting of (a) agents that protect the coating material or treatment composition against UV light, (b) agents that protect the coating material or treatment composition against aging, (c) colorants, (d) decorative agents, (e) agents that promote adhesion for the rest of the coating material or treatment composition, and (f) hydrophobicization agents; and
   (v) a sufficient amount of water for the coating material or treatment composition to be in liquid form, said coating material or treatment composition being storage-stable, being transparent unless made non-transparent by said optional colorant or decorative agent, and having an absence of any organic solvent.

2. The coating material or treatment composition according to claim 1, wherein from 5 to 25 percent of binder (i) is present.

3. The coating material or treatment composition according to claim 1, wherein from 1 to 10 percent of biocidal component (ii) is present.

4. The coating material or treatment composition according to claim 1, wherein the coating material or treatment composition includes from 5 to 25 percent of water-emulsifiable binder (i) and from 1 to 10 percent of biocidal component (ii).

5. The coating material or treatment composition according to claim 4, wherein the water-emulsifiable binder (i) is an oxidatively drying oil or an alkyd resin.

6. The coating material or treatment composition according to claim 1, wherein the optional at least one further biocide is present.

7. The coating material or treatment composition according to claim 1, wherein the water-emulsifiable binder (i) is an oxidatively drying oil or alkyd resin.

8. The coating material or treatment composition according to claim 1, wherein the biocidal component (ii) is a quaternary ammonium halide.

9. The coating material or treatment composition according to claim 1, wherein the biocidal component (ii) is a quaternary ammonium salt of an organic acid.

10. A process for preparing the coating material or treatment composition according to claim 1 comprising (a) mixing together water-emulsifiable binder (i), biocidal component (ii), optionally at least one biocidal agent (iii) and optionally at least one auxiliary or additive member (iv) to form a mixture (a), and (b) adding water (v) to mixture (a) to form the coating material or treatment composition.

11. A process for protecting wood, cellulosic substrates or both against biological material destruction, comprising applying the coating material or treatment composition according to claim 1 to the wood, cellulosic substrate or both.

12. The process according to claim 11, wherein the application is achieved by brushing, rolling or spraying the coating material or treatment composition on the wood, cellulosic substrate or both, or by dipping the wood, cellulosic substrate or both in the coating composition or treatment composition.

13. A coating material or treatment composition for protecting wood and/or cellulosic substrates against biological material destruction, consisting of:
   (i) from 2 to 50 percent of a water-emulsifiable binder selected from the group consisting of (a) water-emulsifiable natural oils, (b) water-emulsifiable synthetic oils, (c) water-emulsifiable alkyd resins based on natural oils, (d) water-emulsifiable alkyd resins based on synthetic oils, and (e) mixtures of at least two of binders (a), (b), (c) and (d);
   (ii) from 0.5 to 40 percent of a biocidal component selected from the group consisting of (a) primary amines, (b) salts of component (a), (c) secondary amines, (d) salts of component (c), (e) tertiary amines, (f) salts of component (e), and (g) mixtures of at least two of components (a), (b), (c), (d), (e) and (f), each of components (a), (b), (c), (d), (e), (f) and (g) having at least one alkyl group having 6 to 24 carbon atoms;

(iii) optionally, at least one auxiliary or additive member selected from the group consisting of (a) agents that protect the coating material or treatment composition against UV light, (b) agents that protect the coating material or treatment composition against aging, (c) colorants, (d) decorative agents, (e) agents that promote adhesion for the rest of the coating material or treatment composition, and (f) hydrophobicization agents; and (iv) a sufficient amount of water for the coating material or treatment composition to be in liquid form, said coating material or treatment composition being storage-stable, being transparent unless made non-transparent by said optional colorant or decorative agent, and having an absence of any organic solvent.

14. The coating material or treatment composition according to claim 13, wherein from 5 to 25 percent of binder (i) is present.

15. The coating material or treatment composition according to claim 13, wherein from 1 to 10 percent of biocidal component (ii) is present.

16. The coating material or treatment composition according to claim 13, wherein the coating material or treatment composition includes from 5 to 25 percent of water-emulsifiable binder (i) and from 1 to 10 percent of biocidal component (ii).

17. The coating material or treatment composition according to claim 13, wherein the water-emulsifiable binder (i) is an oxidatively drying oil or an alkyd resin.

18. The coating material or treatment composition according to claim 13, wherein the water-emulsifiable binder (i) is an oxidatively drying oil or alkyd resin.

19. The coating material or treatment composition according to claim 13, wherein the biocidal component (ii) is a $C_{8-18}$-alkylamine, a N-($C_{8-18}$-alkyl)ethylenediamine, a N-($C_{8-18}$-alkyl)propylenediamine, or a N,N-bis(3-aminopropyl)-$C_{8-18}$-alkylamine.

20. The coating material or treatment composition according to claim 13, wherein the biocidal component (ii) is a methyl-$C_{8-18}$-alkylamine or ethyl-$C_{8-18}$-alkylamine.

21. The coating material or treatment composition according to claim 13, wherein the biocidal component (ii) is a dimethyl($C_{8-18}$-alkyl)amine.

22. The coating material or treatment composition according to claim 13, wherein the biocidal component (ii) is a halide of the primary amine, the secondary amine or the tertiary amine.

23. The coating material or treatment composition according to claim 13, wherein the biocidal component (ii) is an organic acid salt of the primary amine, the secondary amine or the tertiary amine.

24. A process for preparing the coating material or treatment composition according to claim 13, comprising (a) mixing together water-emulsifiable binder (i), biocidal component (ii), and optionally at least one auxiliary or additive member (iii) to form a mixture (a), and (b) adding water (iv) to mixture (a) to form the coating material or treatment composition.

25. A process for protecting wood, cellulosic substrates or both against biological material destruction, comprising applying the coating material or treatment composition according to claim 13 the wood, cellulosic substrate or both.

26. The process according to claim 25 wherein the application is achieved by brushing, rolling or spraying the coating material or treatment composition on the wood, cellulosic substrate or both, or by dipping the wood, cellulosic substrate or both in the coating composition or treatment composition.

* * * * *